US005500190A

United States Patent [19]
Andre et al.

[11] Patent Number: 5,500,190
[45] Date of Patent: Mar. 19, 1996

[54] ANION EXCHANGE RESIN COMPOSITIONS CONTAINING ALMOND PASTE FOR TASTE IMPROVEMENT

[75] Inventors: James R. Andre; John A. Colliopoulos, both of Cincinnati, Ohio

[73] Assignee: The Procter & Gamble Company, Cincinnati, Ohio

[21] Appl. No.: 127,285

[22] Filed: Sep. 23, 1993

Related U.S. Application Data

[63] Continuation of Ser. No. 855,327, Mar. 20, 1992, abandoned.

[51] Int. Cl.$^6$ .......................... A61K 31/78; A61K 31/785
[52] U.S. Cl. ...................................... 424/78.1; 424/78.01
[58] Field of Search .............................. 424/78.01, 78.12, 424/78.08, 78.1, 78.16

[56] References Cited

U.S. PATENT DOCUMENTS

| | | | |
|---|---|---|---|
| Re. 32,811 | 12/1988 | Rudin | 424/195.1 |
| 906,709 | 12/1908 | Heintz | 424/195.1 |
| 2,278,464 | 4/1942 | Musher | 167/56 |
| 3,148,114 | 9/1964 | Fahrenbach et al. | 167/55 |
| 3,499,960 | 3/1970 | Macek et al. | 424/33 |

(List continued on next page.)

FOREIGN PATENT DOCUMENTS

| | | | |
|---|---|---|---|
| 144644 | 6/1985 | European Pat. Off. | A23L 1/308 |

(List continued on next page.)

OTHER PUBLICATIONS

Anderson et al., "Hypocholesterolemic Effects of Psyllium Mucilloid for Hypercholesterolemic Men", Fed. Proceed., 46(3), p. 877 (1987).

Anderson et al., "Dietary Fiber: Hyperlipidemia, Hypertension and Coronary Disease", Amer. J. Gastroent., 81, pp. 907–919 (1986).

Fagerberg, "The Effects of a Bulk Laxative (Metamucil®) on Fasting Blood Glucose, Serum Lipids and Other Variables in Constipated Patients with Non–Insulin Dependent Adult Diabetes", Curr. Thera. Res., vol. 31 (2), pp. 166–172 (1982).

Forman et al., "Increased Excretion of Fecal Bile Acids by an Oral Hydrophilic Colloid", Proc. Soc. Exp. Biol. Med., vol. 127, pp. 1060–1063 (1968).

Beher et al., "The Effect of Psyllium Hydrocolloid and Cholestyramine on Hepatic Bile Lipid Composition in Man", Henry Ford Hospital Medical Journal, 21(1), pp. 21–30 (1973).

Merck Index, 10th Edition, published by Merck & Co., Inc. (1983), No. 2182: "Cholestyramine Resin".

Stein, "Management of Hypercholesterolemia, Approach to Diet and Drug Therapy", The American Journal of Medicine, vol. 87 (4A), pp. 20S–27S (1989).

Questran® (Bristol–Myers) and Cholybars® (Parke Davis), Physicians Desk Reference, 44th Edition, pp. 726–729 and 1595–1597 (1990).

Metamucil®, sold by The Procter & Gamble Company, Physician's Desk Reference for Non–Prescription Drugs, 9th Edition (1988); Medical Economics Company Inc., pp. 642–644.

Goodman and Gilman, The Pharmacologic Basis of Therapeutics, 6th Edition, 1004 and 1007 (1980).

Garvin et al., Proc. Soc. Exp. Biol. Med., 120, 744–746 (1965); Naturacil®, sold by Mead Johnson.

Eat'n Lose® (Peanut Butter) Nutrition Bars, distributed by CCA Industries, Inc. Erasmus Udo, Fat and Oils, 1986 (Alive, Vancouver, Canada) p. 204.

*Primary Examiner*—Peter F. Kulkosky
*Attorney, Agent, or Firm*—Mary Catherine Poland; Kathleen M. Harleston; Douglas C. Mohl

[57] ABSTRACT

The present invention relates to marzipan-like compositions comprising an anion exchange resin, almond paste, and preferably psyllium fiber, in unit dose form. This invention also relates to the use of these compositions in a method for treating hypercholesterolemia. The compositions are a convenient, portable, highly palatable, and well tolerated dosage form for administering anion exchange resin.

25 Claims, No Drawings

U.S. PATENT DOCUMENTS

| | | | |
|---|---|---|---|
| 3,923,972 | 12/1975 | Fields et al. | 424/78 |
| 3,974,272 | 8/1976 | Polli et al. | 424/78 |
| 4,089,981 | 5/1978 | Richardson | 426/104 |
| 4,156,021 | 5/1979 | Richardson | 426/104 |
| 4,315,954 | 2/1982 | Kuipers et al. | 426/583 |
| 4,321,263 | 3/1982 | Powell et al. | 424/195 |
| 4,348,379 | 9/1982 | Kowalsky et al. | 424/34 |
| 4,459,280 | 7/1984 | Colliopoulos et al. | 424/35 |
| 4,511,561 | 4/1985 | Maddaus et al. | 424/195.1 |
| 4,548,806 | 10/1985 | Colliopoulos et al. | 424/35 |
| 4,551,331 | 11/1985 | Rudin | 424/195.1 |
| 4,565,702 | 1/1986 | Morley et al. | 426/93 |
| 4,568,557 | 2/1986 | Becker et al. | 426/618 |
| 4,619,831 | 10/1986 | Sharma | 426/93 |
| 4,639,367 | 1/1987 | Mackles | 424/45 |
| 4,668,519 | 5/1987 | Dartey | 426/548 |
| 4,673,578 | 6/1987 | Becker et al. | 426/93 |
| 4,678,672 | 7/1987 | Dartey et al. | 426/19 |
| 4,698,232 | 10/1987 | Sheu et al. | 426/572 |
| 4,737,364 | 4/1988 | Kalogris | 424/195.1 |
| 4,747,881 | 5/1988 | Shaw et al. | 106/209 |
| 4,766,004 | 8/1988 | Moskowitz | 426/658 |
| 4,778,676 | 10/1988 | Yang et al. | 424/79 |
| 4,784,861 | 11/1988 | Gori | 426/74 |
| 4,790,991 | 12/1988 | Shaw et al. | 424/441 |
| 4,818,539 | 4/1989 | Shaw et al. | 424/441 |
| 4,824,672 | 4/1989 | Day et al. | 424/195.1 |
| 4,828,842 | 5/1989 | Furst et al. | 424/480 |
| 4,843,098 | 6/1989 | Shaw et al. | 514/778 |
| 4,849,222 | 7/1989 | Broaddus | 424/195.1 |
| 4,871,557 | 10/1989 | Linscott | 426/93 |
| 4,882,157 | 11/1989 | Yang et al. | 424/78.12 |
| 4,883,788 | 11/1989 | Day et al. | 514/57 |
| 4,895,723 | 6/1990 | Amer et al. | 424/78.12 |
| 4,931,280 | 6/1990 | Wood et al. | 424/439 |
| 4,950,140 | 8/1990 | Pflaumer et al. | 424/439 |
| 4,950,689 | 8/1990 | Yang et al. | 514/777 |
| 4,981,698 | 1/1991 | Cherukuri et al. | 426/5 |
| 4,996,051 | 2/1991 | Meer et al. | 424/195.1 |
| 5,009,916 | 4/1991 | Colliopoulos et al. | 426/615 |
| 5,013,716 | 5/1991 | Cherukuri et al. | 424/439 |
| 5,015,477 | 5/1991 | Wood et al. | 424/439 |
| 5,023,245 | 6/1991 | Kuhrts | 514/54 |
| 5,048,760 | 9/1991 | Barbera et al. | 241/9 |
| 5,173,296 | 12/1992 | Andre et al. | 424/195.1 |

FOREIGN PATENT DOCUMENTS

| | | | |
|---|---|---|---|
| 285201 | 10/1988 | European Pat. Off. | A61K 35/78 |
| 306469 | 3/1989 | European Pat. Off. | A23L 1/305 |
| 323666 | 7/1989 | European Pat. Off. | A61K 31/785 |
| 362926 | 4/1990 | European Pat. Off. | A61K 35/78 |
| 387933 | 9/1990 | European Pat. Off. | A23L 1/308 |
| 412604 | 2/1991 | European Pat. Off. | A23L 1/00 |
| 6888M | 6/1969 | France | |
| 2430509 | 1/1976 | Germany | A61K 45/08 |
| 249634 | 9/1987 | Germany | A61K 31/785 |
| 63/264534 | 11/1988 | Japan | A61K 45/08 |
| 1446352 | 8/1976 | United Kingdom | A61K 31/74 |
| 1590507 | 6/1981 | United Kingdom | A23L 1/00 |
| 80/00658 | 4/1980 | WIPO | A61K 9/00 |
| WO-A-9211019 | 7/1992 | WIPO | A61K 35/78 |

ANION EXCHANGE RESIN COMPOSITIONS CONTAINING ALMOND PASTE FOR TASTE IMPROVEMENT

This is a continuation of application Ser. No. 855,327, filed on Mar. 20, 1992 now abandoned.

BACKGROUND

This invention relates to novel marzipan-like compositions in unit dosage form containing an anion exchange resin. These compositions comprise almond paste and an anion exchange resin (e.g. cholestyramine, colestipol). An optional, preferred ingredient is psyllium.

Although effective in reducing serum cholesterol, anion exchange resins such as cholestyramine and colestipol have an unpleasant taste and mouthfeel. The present invention compositions greatly improve the aesthetics of these anion exchange resins. These compositions have excellent texture, mouthfeel and palatability, and are well tolerated by the intestinal tract.

High blood cholesterol levels are associated with life threatening cardiac diseases. Cholestyramine and colestipol are drugs used in treating hypercholesterolemia. These drugs are known as basic anion exchange resins. They help to lower blood cholesterol levels apparently by binding to bile acids in the intestine. It is believed that this in turn causes an increase in hepatic metabolism of cholesterol to replenish the bile acids lost to complexation with the anion exchange resins.

Cholestyramine is usually dosed using from four to thirty-two grams, given once daily or divided into two, three, or four equal intervals. At the present time cholestyramine is commercially available as Questran® (manufactured by the Mead Johnson division of Bristol-Myers Company) in a four gram unit dose powder packet or in bulk powder, and as Cholybars® (manufactured by Parke Davis) wherein one chewable bar contains four grams of cholestyramine. [*Physicians Desk Reference*, 44th Edition, pages 726–729 and 1595–1597 (1990).]

Colestipol is usually administered daily in two to four equally divided doses of fifteen to thirty grams. Colestipol is commercially available under the tradename Colestid® (colestipol hydrochloride granules, manufactured by The Upjohn Company). It is sold in a five gram unit dose powder packet or in bulk powder. [*Physicians Desk Reference*, 44th Edition, pages 433 and 2216–2218 (1990)].

While the benefits of anion exchange resins are well known and appreciated, the aesthetics (e.g., mouthfeel; taste; throat sticking) are considered by many users to be very unpleasant. Cholestyramine can give the perception of sticking to the back of the mouth and throat upon ingestion, and may be viewed as leaving a fishy taste in the mouth. Colestipol has an astringent taste and a sandy, gritty texture which sticks to the mouth and teeth after ingestion. Obviously, poor aesthetics raise concern about how closely patients will comply with any treatment regimen involving these drug therapies.

Several attempts have been made to improve the palatability of anion exchange resins. Patents which disclose such attempts include: East German Patent DD 249,634 published Sep. 16, 1987 by V&B Chemukombinat Bitterfeld (describes grinding a basic anionic exchanger such as cholestyramine in a wet state and spraying on an aqueous solution of pectin during drying); Great Britain Patent Specification Number 1,446,352, published Aug. 18, 1976 by Merck & Co., Inc. (describes an oral pharmaceutical composition in liquid form comprising a coacervate of a hydrophilic colloid of a cellulose derivative, such as sodium carboxymethyl cellulose, and cholestyramine); French Medical Patent 6,888 M published Jun. 4, 1964 by Mead Johnson & Company (describes dry mixing acacia gum with cholestyramine resin to aid in making the extreme astringency of cholestyramine disappear); U.S. Pat. No. 4,895,723, issued to Amer et al. Jan. 23, 1990 (describes orally ingestible compositions for reduction of blood cholesterol levels comprising cholestyramine and a water-soluble carbohydrate syrup such as high fructose corn syrup or a liquid alcohol polyol humectant such as glycerine); U.S. Pat. No. 4,843,098, issued to Shaw et al. Jun. 27, 1989, U.S. Pat. No. 4,818,539, issued to Shaw et al. Apr. 4, 1989, and U.S. Pat. No. 4,790,991, issued to Shaw et al. Dec. 13, 1989, divisions of U.S. Pat. No. 4,747,881, issued to Shaw et al. May 31, 1988 (relating to preswelled substantially anhydrous hydrocolloid aggregate such as carboxymethyl cellulose with a size range of about 4 to about 70 U.S. mesh, and a substrate comprising dietary fiber and/or drug, such as cholestyramine); U.S. Pat. No. 4,778,676, issued to Yang et al. Oct. 18, 1988 (describes a chewable delivery system for actives comprising an active, such as cholestyramine, precoated with at least one material selected from the group consisting of lecithin, polyoxyalkenes having chain lengths of about four carbons or less, glycerides having a melting point of 100° C. or less, polyalkylene glycols having a molecular weight of 3,700 or less, synthetic and natural waxes and mixtures thereof, and a confectionery matrix comprising a binder system of gelatin and a humectant material); U.S. Pat. No. 3,974,272, issued to Polli et al. Aug. 10, 1976 (describes a palatable oral coacervate composition containing cholestyramine and a modified gum selected from the group consisting of hydrophillic colloid of cellulosive material and charged anionic gum in an aqueous medium); and U.S. Pat. No. 3,499,960, issued to Macek et al. (describes coating the cholestyramine particles with an acrylic polymer crosslinked with allylsucrose).

Other publications relating to therapeutic use of cholestyramine or psyllium include the following. European Patent Application Publication No. 323,666, published Jul. 12, 1989 by The Procter & Gamble Company. This publication describes methods and compositions for reducing blood cholesterol levels by oral administration of psyllium and cholestyramine, optionally in combination with polyol polyesters. It is also stated therein that "cholestyramine resin, administered orally, has sometimes been associated with constipation and preparations containing cholestyramine often have an unpleasant sandy or gritty quality. Advantageously, these problems associated with cholestyramine are alleviated when the psyllium and/or psyllium plus optional polyol polyesters are employed therewith."

U.S. Pat. No. 4,824,672, issued to Day et al. Apr. 25, 1989, describes an orally utilizable pharmaceutical composition comprising gel-forming fiber (such as guar gum, psyllium seed, pectin, glucomannan, oat and barley) and a mineral salt (such as calcium carbonate, magnesium carbonate, or potassium carbonate) said to be administered to humans to reduce serum cholesterol levels.

*Management of Hypercholesterolemia. Approach to Diet and Drug Therapy*, Stein, The American Journal of Medicine, Vol. 87(4A) (1989) advises patients who experience constipation from the use of cholestyramine or colestipol (bile acid sequestrants used to decrease blood cholesterol levels) to take a bulk laxative, such as psyllium fiber, with the evening dose of sequestrant if other dietary changes do not alleviate the problem of constipation.

*The Effect of Psyllium Hydrocolloid and Cholestyramine on Hepatic Bile Lipid Composition in Man,* Behrer et al., Henry Ford Hospital Medical Journal, Vol. 21(1) (1973), examined the effects of psyllium hydrocolloid and of cholestyramine on the total cholesterol, total phospholipid, total bile salt, cholate, chenodeoxycholate, and deoxycholate concentrations of 6 post-cholecystectomy patients.

Other U.S. patents that describe compositions in which psyllium is an optional or essential ingredient include: U.S. Pat. No 4,766,004, to Moskowitz, issued Aug. 23, 1988 (describes dietary fiber supplement compositions comprising whole psyllium husks having a particle size of from 12 to 70 mesh, food grade vegetable fat which is a solid at room temperature, sweetening agent and flavoring agent); and U.S. Pat. No. 4,698,232, to Sheu et al., issued Oct. 6, 1987 (describes fiber-containing confectionery compositions comprising dietary fiber pretreated with a lubricant, a foamed matrix, and an amorphous matrix).

Naturacil® (sold by Mead Johnson) is an artificial chocolate flavored, caramel-like laxative product containing psyllium. The ingredients listed for this product include sugar, glycerin, nonfat milk, and partially hydrogenated vegetable oil.

U.S. Pat. No. 4,871,557 to Linscott, issued Oct. 3, 1989 describes a granola bar containing supplemental dietary fiber. Psyllium is listed as one of many sources of supplemental dietary fiber. Flavoring agents, toasted rolled oats, chopped almonds, and coconut flakes are among many materials mentioned as optional granola ingredients. U.S. Pat. No. 4,619,831, to Sharma, issued Oct. 28, 1986, describes dietary fiber products comprising insoluble dietary fiber (92–98.5%) coated or enrobed with soluble dietary fiber (1.5–8%; psyllium is mentioned as one of many soluble fibers). U.S. Pat. No. 5,009,916, to Colliopoulos, issued Apr. 23, 1991, describes high fiber food compositions comprising psyllium and other dietary fiber sources.

West German Patent Specification 2,430,509, published Jan. 15, 1976 by Hypolab S.A., Genf. (Schweiz), describes preparing compositions containing bulk laxatives (including psyllium mucilloid) in the form of a cake. The cake dough is prepared and baked in molds to produce cakes having thickness of 3–6 mm.

Further, U.S. Pat. No. 4,568,557, issued Feb. 4, 1986 and U.S. Pat. No. 4,673,578, issued Jun. 16, 1987, both to Becker et al., describe high dietary fiber-containing snack food products and methods comprising from about 5% to about 30% by weight of dietary fiber, soaked in food grade oil, for example, admixed with peanut butter such that the peanut oil becomes absorbed by the fiber, and further mixed with a compound coating.

Other documents include: U.S. Pat. No. 4,511,561, to Madaus et al., issued Apr. 16, 1985; Goodman & Gilman, The Pharmacologic Basis of Therapeutics, Sixth Edition, 1004 (1980); Garvin et al., *Proc. Soc. Exp. Biol. Med.,* 120, 744–746 (1965); Forman et al., *Proc. Soc. Exp. Biol. Med.,* 127, 1060–1063 (1968); Anderson et al., *Fed. Proc.,* 46, 877 (1987); Anderson et al., *Am. J. Gastroenterol.,* 81, 907–919 (1986); and Fagerberg, *Curr. Ther. Res.,* 31, 166 (1982).

Although a considerable amount of research has been aimed at developing palatable compositions containing an anion exchange resin, a great need still exists for compositions that provide therapeutic benefit while maintaining an agreeable texture and taste, thereby encouraging patient compliance with a prescribed treatment regimen. It has been discovered that combining an anion exchange resin (such as cholestyramine or colestid) in a marzipan composition helps to mask the unpleasant taste and mouthfeel associated with these resins. It has also been discovered that an anion exchange resin can be prepared in the form of a marzipan-like composition with psyllium as a preferred optional ingredient. These compositions are believed to offer an even greater enhancement to the texture, mouthfeel and taste of compositions containing an anion exchange resin, as well as enhanced efficacy.

An object of the present invention is therefore to provide convenient, portable and highly palatable compositions that deliver an anion exchange resin in a marzipan-like medium. Another object of this invention is to provide a method for treating hypercholesterolemia by administering to humans a pharmaceutical composition comprising an anion exchange resin in a marzipan-like composition. A further object of the invention is to enhance the acceptance and compliance with a treatment regimen involving anion exchange resin by hypercholesterolemic patients by improving through the present invention the palatability and overall mouthfeel of compositions containing an anion exchange resin. Another object of the present invention is to provide anion exchange resin treatment for hypercholesterolemia that is more efficacious and/or more readily tolerated by the gastrointestinal tract.

These and other objects of the present invention will become readily apparent from the detailed description which follows.

All percentages and ratios used herein are by weight, and all measurements are made at 25° C., unless otherwise specified.

SUMMARY OF THE INVENTION

The present invention relates anion exchange resin-containing compositions. These compositions comprise: from about 1% to 65% anion exchange resin; from about 5% to about 80% almond paste; from 0% to about 85% carrier material; and, preferably, from about 5% to about 50% psyllium fiber. Furthermore, the compositions preferably have water activities ("Aw") within the range of from about 0.25 to about 0.75. The compositions are in unit dosage form (e.g., bars; wafers).

Additionally, the present invention relates to treating hypercholesterolemia in human or lower animal patients. Said method comprises administering to a human or lower animal patient in need of such treatment a safe and effective amount of a pharmaceutical composition according to the present invention.

DETAILED DESCRIPTION OF THE INVENTION

Anion Exchange Resin-Containing Compositions

The present invention relates to marzipan-like compositions containing an anion exchange resin in unit dosage form. These compositions comprise: (a) an anion exchange resin; (b) almond paste; and (c) preferably, carrier materials suitable for ingestion (preferably sugars and/or humectants and/or flavorants). A preferred optional component is psyllium fiber. Further, these compositions preferably have low water activities ("Aw"). The components for use in the present compositions, and the preferred amounts to be utilized, are described in detail hereinafter.

(a) Anion Exchange Resin:

The term "anion exchange resin", as used herein, means any resinous material having cationic moieties such that the material is safe and therapeutically effective for treating hypercholesterolemia (at a reasonable benefit/risk ratio within the scope of sound medical judgement). Preferred anion exchange resins useful herein include cholestyramine, cholestipol, and mixtures thereof.

Cholestyramine is a strongly basic anion exchange resin which contains quaternary ammonium functional groups attached to a styrene-divinylbenzene copolymer. [*The Merck Index*, 10th Edition, published by Merck & Co., No. 2182 (1983), incorporated by reference herein in its entirety]. Cholestyramine resin-containing compositions are available commercially in powder form under the trade names Cuemid® (Merck, Sharp & Dome) and Questran® (Bristol Laboratories division of Bristol-Myers). Cholestyramine is commercially available as Duolite AP-143 resin (Rohm & Haas Co.).

Colestipol is an insoluble, high molecular weight basic anion-exchange copolymer of diethylene triamine and 1-chloro- 2,3-expoxypropane with approximately 1 out of 5 amine nitrogens protonated (chloride form). [*The Merck Index*, 11th edition, published by Merck & Co., No. 2472 (1989), incorporated by reference herein in its entirety]. Colestipol is commercially available as colestipol hydrochloride granules under the trade name Colestid® (Upjohn).

The anion exchange resin in the present invention compositions typically comprises from about 1% to about 65% by weight of the pharmaceutical composition of the present invention, and preferably from about 5% to about 50%. Most preferred is the anion exchange resin comprising from about 10% to about 30% by weight of the pharmaceutical composition of the present invention.

(b) Almond Paste:

The present invention also comprises almond paste as it is typically prepared and used in marzipan compositions. Almond paste is commercially available, being sold, for example, by Blue Diamond, Sacramento, Calif. [e.g., Blanched Almond Paste, Item Code 0787, having the ingredients: blanched almonds (58%), sugar (27.5%), water (12.5–16.5%), potassium sorbate (0.22%), natural almond oil flavoring or artificial flavoring (0.14%), and polysorbate 80 (0.003%)].

For purposes of the present invention, the almond paste should comprise at least about 10% of ground almond, preferably from about 10% to about 65% of ground almond, and more preferably from about 25% to about 60% of ground almond, by weight of the almond paste. The majority of the remaining portion of the almond paste is one or more sweetening agents, and typically in an amount from about 20% to about 75%, and preferably from about 20% to about 40%, by weight of the almond paste. Almond paste and marzipan compositions are described in more detail in: Sugar Confectionery and Chocolate Manufacture, by R. Lees and E. B. Jackson (Leonard Hill; copyright 1973), pages 103–105 and 337–339; and Chocolate, Cocoa, and Confectionery: Science and Technology, 2nd Edition, by B. W. Minifie, (The AVI Publishing Company, Inc.; copyright 1980), pages 442–445, the disclosures of which are incorporated herein by reference in their entirety.

Compositions of the present invention typically comprise from about 5% to about 80% almond paste, preferably from about 5% to about 45% almond paste, and more preferably from about 5% to about 40% almond paste, by weight of the anion exchange resin-containing compositions.

(c) Carrier Materials Suitable for Ingestion:

The compositions of the present invention may further comprise other components compatible with the anion exchange resin and almond paste, and which are suitable for ingestion. In particular, such components must not significantly reduce the therapeutic efficacy of the anion exchange resin. Compositions of the present invention typically comprise from 0% to about 85% of one or more carrier materials suitable for ingestion, preferably from about 25% to about 70% and more preferably from about 30% to about 60% by weight of the compositions.

The present compositions preferably comprise a sweetening agent in addition to any sweetening agent provided as part of the almond paste. This includes water-soluble sweetening agents such as monosaccharides, disaccharides, and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol and mixtures thereof. Sugar components also include materials such as invert sugar syrups, brown sugar, honey, molasses, maple syrup and the like. Sugar components may also be very fine particle size sucrose and/or fructose, and/or corn syrup solids, such as powdered (10X) sugar.

For purposes of the present invention, it is possible to use a non-nutritive artificial sweetener (e.g., aspartame, sold as Nutrasweet® brand sweetener by G. D. Searle; saccharin; cyclamate) for some or all of the sweetening agent component of the carrier material. This is particularly preferred when the present composition is to be taken by persons on a restricted caloric diet, or is to be taken for extended periods of time.

Examples of artificial sweeteners include saccharin, cyclamate, acesulfame K (American Hoechst), Gem Sweet (Cumberland Packing Corp.), L-sugars (Lev-O-Cal Biospherics), Hernandulcin (University of Illinois), alitame (Pfizer), Thaumatins, trichloro sucrose, Rebaudioside A, L-aspartyl-L-phenylalanine methyl ester, aspartyl-D-valine isopropyl ester, aspartyl amino malonates, dialkyl aspartyl aspartates, stevioside, glycyrrhizin, p-phenetylurea, 5-nitro-2-propoxyaniline and neohesperidin dihydrochalcone. The term L-aspartyl-L-phenylalanine methyl ester and methyl L-aspartyl-L-phenylalanine are used interchangeably and correspond to the compound also known as aspartame. Preferred artificial sweeteners are saccharin, cyclamate, acesulfame K, and especially aspartame.

The compositions of the present invention preferably comprise from about 1% to about 65% of such additional sweetening agents, and more preferably from about 10% to about 40% of such sweetening agents by weight of the compositions.

The present compositions also preferably comprise a humectant, preferably glycerin which also provides benefits as a mixing aid and helps keep the Aw of the compositions lower. Food grade quality glycerin is commercially available. Glycerin preferably comprises from about 1% to about 20% of the present compositions, and preferably from about 3% to about 10%.

The present compositions also optionally comprise dietary fiber, preferably psyllium husk fiber as described hereinafter and/or insoluble dietary fiber. The term "insoluble dietary fiber", as used herein, means the water insoluble, substantially non-swellable component of fiber material safe for human ingestion which is non-digestible and non-metabolizable by humans.

A wide range of materials containing insoluble dietary fiber may be used in the present invention. Preferred are cereal brans and mixtures thereof, due to their relatively high content of insoluble dietary fiber. Also preferred is that these cereal brans comprise at least about 75% of the insoluble dietary fiber. Brans preferred include those selected from the group consisting of wheat, corn, barley, rye, oats, rice, soybean, beets, and mixtures thereof. Most preferred are oat or corn. The components of the insoluble dietary fiber from these cereal brans are known to be cellulose, hemicellulose and lignin.

Compositions of the present invention containing insoluble dietary fiber typically comprise from about 1% to about 20% of an insoluble dietary fiber, and preferably from about 5% to about 10% insoluble dietary fiber, by weight of the compositions.

Other optional components which may be included are milk products such as whole milk, skim milk, buttermilk, whey, concentrated milk product (condensed or evaporated milk), dried milk products, nonfat milk powder, dry whole milk, modified whole milk and the like, egg products, including egg whites and egg yolks, protein sources (e.g., soy protein), spices, cocoa powder, flavorants such a vanilla, salt, color additives, preservatives (preferably sorbic acid), polyhydric alcohols such as glycerol and propylene glycol, emulsifiers such as lecithin or modified lecithin, antioxidants such as ascorbic acid and alpha-tocopherol, and the like. It is also possible to coat the anion exchange resin-containing compositions of the present invention with a variety of confectionary coating materials. Preferred is coating the entire composition (i.e., enrobing) with from about 10% to about 30% of a coating material, preferably a confectionery coating material, by weight of the final coated anion exchange resin-containing composition.

In addition, mainly for storage stability purposes, the compositions of the present invention are preferably formulated to have water activities ("Aw") in the range of about 0.25 to about 0.75. Levels above this range are generally not desirable, especially when psyllium husk fiber is utilized as part of the composition, unless consumption is to occur within a relatively short time after preparation. Levels below this range are generally perceived as giving too dry a mouthfeel. Aw is a well-known property in the art (see, for example, "Water Activity and Food" by Troller and Christian (Academic Press, N.Y.; 1978) incorporated by reference herein in its entirety) and Aw can be measured by commercially available instruments.

Finally, the compositions of the present invention are in unit dosage forms. Typically, these unit dosage forms are bars or wafers, generally prepared by forming or molding the compositions into the desired form. These unit dosage forms are generally of a size and shape suited for ingesting by chewing, so as to administer the therapeutically effective amount of anion exchange resin by a minimum number of dose units.

(d) Psyllium Fiber:

The present compositions preferably comprise psyllium fiber. The term "psyllium fiber", as used herein, means the seed coat or "husk" of psyllium seed (either intact or macerated or otherwise comminuted).

Psyllium fiber comes from psyllium seed, from plants of the Plantago genus. Various species such as *Plantago lanceolate, P. rugelii,* and *P. major,* are known. Commercial psyllium includes the French (black; *Plantago indica*), Spanish (*P. psyllium*) and Indian (blonde; *P. ovata*). Indian (blonde) psyllium is preferred for use herein.

Intact or macerated seeds can be used in the practice of this invention. However, it is typical to remove the seed coats from the rest of the seed by, for example, slight mechanical pressure, and then to use only the seed coat. In the practice of the present invention it is convenient and desirable to use macerated seed coat. The seed coat is therefore preferably removed and sanitized by methods known in the art prior to use in the present compositions. For example, the psyllium husk may be sanitized by ethylene oxide or, preferably, by superheated steam (as described in U.S. Pat. No. 4,911,889, issued Mar. 27, 1990 to Leland et al., incorporated herein by reference in its entirety). Furthermore, the psyllium fiber preferably has high purity, being about 85% to about 100% pure, and more preferably being about 95% to about 100% pure.

The preferred compositions of the present invention comprise from about 5% to about 50% psyllium fiber, preferably from about 5% to about 30% psyllium fiber, and more preferably from about 10% to about 25% psyllium fiber, by weight of the compositions.

Method of Treatment

The method of treatment herein comprises orally administering to a human or lower animal patient in need of having a lowered blood cholesterol level a safe and effective amount of an anion exchange resin-containing composition according to the present invention, preferably also comprising psyllium fiber. The term "safe and effective amount", as used herein, means an amount of an anion exchange resin, or anion exchange resin/psyllium fiber, composition high enough to significantly positively modify the hypercholesterolemic condition being treated, but low enough to avoid serious side effects (at a reasonable benefit/risk ratio), within the scope of sound medical judgement. The safe and effective amount will vary with the age and physical condition of the patient being treated, the severity of the condition, the duration of treatment, the nature of concurrent therapy, and like factors within the knowledge and expertise of the of the attending physician. However, a patient in need of such treatment will typically receive from 4 g to about 30 g of the anion exchange resin daily and, if present, from 1 g to 30 g of psyllium husk.

Treatment of the human or lower animal patient comprises continuous administration of the anion exchange resin compositions, or anion exchange resin/psyllium compositions, to lower and/or maintain lowered cholesterol levels. As used herein "continuous administration" means ingestion by a human in need of said treatment one or more doses a day of an anion exchange resin (and preferably psyllium) for two or more days. Daily ingestion of the present compositions preferably comprises from about 4 g to about 24 g of the anion exchange resin and from about 5 g to about 15 g psyllium husk taken orally, with said ingestion being once daily or at two, three, or four regularly spaced intervals throughout the day. It may also be beneficial to administer said dose in relationship to meals, preferably prior to a meal, and at bedtime.

The following examples further describe and demonstrate embodiments within the scope of the present invention. The examples are given solely for the purpose of illustration and are not to be construed as limitations of the present invention as many variations thereof are possible without departing from the spirit and scope.

EXAMPLE 1

| Ingredients | Weight % |
| --- | --- |
| Psyllium[1] | 13.86 |
| Almond Paste[2] | 13.86 |
| Corn Syrup[3] | 22.71 |
| Powdered Sugar[4] | 4.40 |
| Glycerin | 8.19 |
| Ground Cinnamon | 0.94 |
| Sorbic Acid | 0.08 |
| Nutmeg | 0.08 |
| Sorbitol Crystaline | 12.60 |
| Cholestyramine Resin[5] | 11.05 |
| Yogurt Coating[6] | 12.23 |

[1]Steam sanitized psyllium fiber (95% purity).
[2]Blanched almond paste (unflavored), by Blue Diamond (Sacramento, Calif., Item Code 0787): 58% blanched almonds, 27.5% sugar, 12.5–16.5% water, 0.22% potassium sorbate, and 0.003% polysorbate 80, without the 0.14% almond oil flavoring.
[3]80% solids.
[4]98% Sucrose, 2% corn starch; 10X powder.
[5]Duolite AP-143 resin (Rohm & Haas Co., Philadelphia, Pennsylvania).
[6]Yogurt flavored confectionery coating, Product Code 9155, by Shade Foods, Inc. (Belmont, California) having an ingredients list of sugar, partially hydrogenated vegetable oil (containing one or more of the following: coconut, palm kernel, cottonseed, palm, soybean), nonfat yogurt solids, lecithin, artificial color, vanillin, and salt.

The present compositions are prepared by the following procedure. Break the almond paste into small pieces and transfer into a Hobart mixer. Heat the high fructose corn syrup to 83 brix. Add high fructose corn syrup premixed with sorbic acid, glycerine, spices (cinnamon and nutmeg), and mix for 1 minute. Add all dry materials (powdered sugar, psyllium, sorbitol, and cholestyramine) and mix for 2 minutes or until a homogenous mixture is achieved. Scrape the Hobart mixer and mix for 1 minute. Roll the dough into desired thickness and cut into pieces of about 22.5 grams. Enrobe these pieces with about 3 grams of the yogurt coating after melting the yogurt coating until liquid in a microwave oven using low heat (not heated over 110° F., 43° C.). Place in a refrigerator to cool for about 10 minutes. The Aw of this composition is approximately 0.482.

Ingestion of one piece of this product delivers 2.71 grams of cholestyramine and 3.4 grams of psyllium for use in the treatment of hypercholesterolemia. The psyllium also aids in normalizing the possible constipating effect of cholestyramine.

EXAMPLE 2

| Ingredients | Weight % |
| --- | --- |
| Psyllium | 12.30 |
| Powdered Sugar | 5.10 |
| Corn Syrup | 20.14 |
| Almond Paste | 8.93 |
| Glycerin | 7.27 |
| Sorbic Acid | 0.07 |
| Peanut Paste[1] | 13.42 |
| Peanut Butter Flavor | 0.29 |
| Sorbitol Crystaline | 9.51 |
| Colestid @[2] | 12.12 |
| Chocolate Coating | 10.85 |

[1]Roasted peanuts, milled into a paste.
[2]Sold by the Upjohn Company (Kalamazoo, Michigan), wherein 5 grams of powder mix supplies 5 grams of colestipol hydrochloride granules.

This composition is prepared by a method similar to the procedure in Example 1 except that the peanut paste is added with the almond paste in the Hobart mixer. The peanut butter flavor is premixed with the heated high fructose corn syrup, sorbic acid and glycerine and mixed for 1 minute. The dough is cut into pieces of 24.7 grams. The pieces are enrobed in a chocolate coating in which chocolate is melted and prepared by the same procedure as the yogurt coating in Example 1. The Aw of this composition is approximately 0.422.

Ingestion of one piece of this product delivers 3.35 grams of colestipol granules and 3.4 grams of psyllium for use in the treatment of hypercholesterolemia. The psyllium aids in normalizing the possible constipating effect of colestid.

EXAMPLE 3

| Ingredients | Weight % |
| --- | --- |
| Sorbitol Crystaline | 15.18 |
| Glycerin | 9.88 |
| Almond Paste | 16.71 |
| Corn Syrup | 17.20 |
| Powdered Sugar | 5.31 |
| Sorbic Acid | 0.10 |
| Ground Cinnamon | 1.12 |
| Nutmeg | 0.10 |
| Cholestyramine | 19.66 |
| Yogurt Coating | 14.74 |

This composition is prepared by the same method used in Example 1. The dough is cut into pieces of 17.4 grams, and enrobed in the yogurt coating described in Example 1.

Ingestion of one piece of this product delivers 4.00 grams of cholestyramine in a composition that is pleasant tasting and convenient.

What is claimed is:

1. A palatable composition of improved taste and mouthfeel as compared to the same composition not containing almond paste comprising:

(a) from about 1% to about 65% anion exchange resin;

(b) from about 5% to about 80% almond paste wherein said almond paste comprises ground almond, and one or more sweetening agents;

(c) from about 0% to about 85% carrier materials suitable for ingestion, and wherein further said composition is in a unit dose form.

2. The composition according to claim 1 wherein the anion exchange resin is selected from the group consisting of cholestyramine, colestipol and mixtures thereof.

3. The composition according to claim 1 wherein the almond paste comprises from about 10% to about 65% of ground almond by weight of the almond paste.

4. The composition according to claim 3 wherein the almond paste further comprises from about 20% to about 75% of one or more sweetening agents by weight of the almond paste.

5. The composition according to claim 4 comprising from about 25% to about 70% carrier materials suitable for ingestion, and wherein further said carrier materials comprise one or more ingestible materials selected from the group consisting of glycerin, sweetening agents, flavorants, preservatives, and mixtures thereof.

6. The composition according to claim 5 wherein the carrier materials comprise from about 1% to about 20% glycerin and from about 1% to about 65% of one or more sweetening agents, by weight of the composition.

7. The composition according to claim 6 having an Aw within the range of from about 0.25 to about 0.75.

8. The composition according to claim 1 further comprising a safe and effective amount of psyllium fiber.

9. A palatable composition of improved taste and mouthfeel as compared to the same composition not containing almond paste comprising:
   (a) from about 1% to about 65% anion exchange resin;
   (b) from about 5% to about 80% almond paste wherein said almond paste comprises blanched almonds, sugar, and water;
   (c) from about 0% to about 85% carrier materials suitable for ingestion; and
   (d) from about 5% to about 50% psyllium fiber,
   and wherein further said composition is in a unit dose form.

10. The composition according to claim 9 wherein the anion exchange resin is selected from the group consisting of cholestyramine, colestipol and mixtures thereof.

11. The composition according to claim 9 wherein the almond paste comprises from about 10% to about 65% of ground almond by weight of the almond paste.

12. The composition according to claim 11 wherein the almond paste further comprises from about 20% to about 75% of one or more sweetening agents by weight of the almond paste.

13. The composition according to claim 12 comprising from about 25% to about 70% carrier materials suitable for ingestion, and wherein further said carrier materials comprise one or more ingestible materials selected from the group consisting of glycerin, sweetening agents, flavorants, preservatives, and mixtures thereof.

14. The composition in claim 13 wherein the carrier materials comprise from about 1% to about 20% glycerin and from about 1% to about 65% of one or more sweetening agents, by weight of the composition.

15. The composition according to claim 14 having an Aw within the range of from about 0.25 to about 0.75.

16. A palatable composition of improved taste and mouthfeel as compared to the same composition not containing almond paste comprising:
   (a) from about 5% to about 50% anion exchange resin;
   (b) from about 5% to about 45% almond paste, wherein said almond paste comprises from about 10% to about 65% ground almond, and from about 20% to about 75% of one or more sweetening agents, by weight of almond paste; and
   (c) from about 25% to about 70% of carrier materials suitable for ingestion selected from the group consisting of glycerin, sweetening agents, flavorants, preservatives, and mixtures thereof;
   (d) from about 5% to about 30% psyllium fiber,
   and wherein further said composition is in a unit dose form.

17. The composition according to claim 16 wherein the anion exchange resin is selected from the group consisting of cholestyramine, colestipol and mixtures thereof.

18. The composition according to claim 17 comprising from about 3% to about 10% glycerin, and said composition has an Aw within the range of from about 0.25 to about 0.75.

19. The composition according to claim 18 wherein the almond paste comprises from about 20% to about 40% of one or more sweetening agents, by weight of the almond paste, and wherein further the carrier material comprises from about 10% to about 40% of one or more sweetening agents, by weight of the composition.

20. A palatable composition of improved taste and mouthfeel as compared to the same composition not containing almond paste comprising:
   (a) from about 10% to about 30% anion exchange resin;
   (b) from about 5% to about 40% almond paste, wherein said almond paste comprises from about 25% to about 60% ground almond and from about 20% to about 40% of one or more sweetening agents, by weight of almond paste;
   (c) from about 3% to about 10% glycerin;
   (d) from about 30% to about 60% of carrier material suitable for ingestion selected from the group consisting of sweetening agents, flavorants, preservatives, and mixtures thereof, and wherein further said carrier material comprises from about 10% to about 40% of one or more sweetening agents by weight of the composition; and
   (e) from about 10% to about 25% psyllium fiber;
   and wherein further said composition has an Aw within the range of from about 0.25 to about 0.75, and is in a unit dose form.

21. The composition according to claim 20 further coated with from about 10% to about 30% of a confectionery coating.

22. A method for reducing serum cholesterol levels in a human or lower animal patient, said method comprising administering to a human or lower animal in need of such treatment a safe and effective amount of an anion exchange resin-containing composition according to claim 1.

23. A method for reducing serum cholesterol levels in a human or lower animal patient, said method comprising administering to a human or lower animal in need of such treatment a safe and effective amount of a psyllium and anion exchange resin-containing composition according to claim 9.

24. A method for reducing serum cholesterol levels in a human or lower animal patient, said method comprising administering to a human or lower animal in need of such treatment a safe and effective amount of a psyllium and anion exchange resin-containing composition according to claim 16.

25. A method for reducing serum cholesterol levels in a human or lower animal patient, said method comprising administering to a human or lower animal in need of such treatment a safe and effective amount of a psyllium and anion exchange resin-containing composition according to claim 20.

* * * * *